US007948630B2

(12) United States Patent
Adam et al.

(10) Patent No.: US 7,948,630 B2
(45) Date of Patent: May 24, 2011

(54) AUTO FOCUS OF A WORKPIECE USING TWO OR MORE FOCUS PARAMETERS

(75) Inventors: Norton Adam, Palo Alto, CA (US); Xinkang Tian, San Jose, CA (US)

(73) Assignee: Tokyo Electron Limited, Tokyo (JP)

( * ) Notice: Subject to any disclaimer, the term of this patent is extended or adjusted under 35 U.S.C. 154(b) by 196 days.

(21) Appl. No.: 12/247,867

(22) Filed: Oct. 8, 2008

(65) Prior Publication Data
US 2010/0085576 A1   Apr. 8, 2010

(51) Int. Cl.
*G01N 21/55* (2006.01)
(52) U.S. Cl. .................. 356/445; 356/499; 356/521
(58) Field of Classification Search .......... 356/499, 356/500, 508–510, 521, 445–448, 237.1–237.5
See application file for complete search history.

(56) References Cited

U.S. PATENT DOCUMENTS

| | | | |
|---|---|---|---|
| 6,778,273 B2 | 8/2004 | Norton et al. | |
| 6,785,638 B2 | 8/2004 | Niu et al. | |
| 6,891,626 B2 | 5/2005 | Niu et al. | |
| 6,943,900 B2 | 9/2005 | Jakatdar et al. | |
| 6,950,188 B2 * | 9/2005 | Wu et al. | 356/401 |
| 7,280,229 B2 | 10/2007 | Li et al. | |
| 7,660,696 B1 | 2/2010 | Norton et al. | |
| 7,831,528 B2 | 11/2010 | Doddi et al. | |
| 2005/0192914 A1 | 9/2005 | Drege et al. | |
| 2005/0209816 A1 | 9/2005 | Vuong et al. | |

OTHER PUBLICATIONS

Automatic focus Control: the astigmatic lens approach, Cohen et al, Applied Optics, vol. 23, No. 4, 1984.*
U.S. Appl. No. 12/050,053, filed Mar. 17, 2008 for Tian et al.
U.S. Appl. No. 12/050,919, filed Mar. 18, 2008 for Tian et al.
U.S. Appl. No. 12/057,316, filed Mar. 27, 2008 for Tian et al.
U.S. Appl. No. 12/057,332, filed Mar. 27, 2008 for Tian et al.
U.S. Appl. No. 12/057,346, filed Mar. 27, 2008 for Tian et al.
U.S. Appl. No. 12/059,610, filed Mar. 31, 2008 for Meng et al.
U.S. Appl. No. 12/141,754, filed Jun. 18, 2008 for Tian et al.
U.S. Appl. No. 12/141,867, filed Jun. 18, 2008 for Tian et al.
U.S. Appl. No. 12/141,892, filed Jun. 18, 2008 for Tian et al.
U.S. Appl. No. 12/242,839, filed Sep. 30, 2008 for Mihaylov.

* cited by examiner

*Primary Examiner* — Michael P Stafira
*Assistant Examiner* — Jonathon D Cook
(74) *Attorney, Agent, or Firm* — Manuel B. Madriaga

(57) ABSTRACT

Provided is a method for focusing a workpiece in the Z-axis for optical metrology. The auto focusing subsystem includes a focus detector having a tilt angle, a capture range, and a plurality of sensors. A processor coupled to the focus detector is configured to utilize the plurality of focus signals measured using the focus detector to determine two or more focus parameters. The two or more focus parameters and calibration data are used to determine an initial position of the workpiece and to generate instructions to move the workpiece to a best focus position.

19 Claims, 9 Drawing Sheets

US 7,948,630 B2

AUTO FOCUS OF A WORKPIECE USING TWO OR MORE FOCUS PARAMETERS

BACKGROUND

1. Field

The present application generally relates to the design of an optical metrology system to measure a structure formed on a workpiece, and, more particularly, to a method and an apparatus for auto focusing the workpiece in the optical metrology system.

2. Related Art

Optical metrology involves directing an incident beam at a structure on a workpiece, measuring the resulting diffraction signal, and analyzing the measured diffraction signal to determine various characteristics of the structure. The workpiece can be a wafer, a substrate, photomask or a magnetic medium. In manufacturing of the workpieces, periodic gratings are typically used for quality assurance. For example, one typical use of periodic gratings includes fabricating a periodic grating in proximity to the operating structure of a semiconductor chip. The periodic grating is then illuminated with an electromagnetic radiation. The electromagnetic radiation that deflects off of the periodic grating are collected as a diffraction signal. The diffraction signal is then analyzed to determine whether the periodic grating, and by extension whether the operating structure of the semiconductor chip, has been fabricated according to specifications.

In one conventional system, the diffraction signal collected from illuminating the periodic grating (the measured diffraction signal) is compared to a library of simulated diffraction signals. Each simulated diffraction signal in the library is associated with a hypothetical profile. When a match is made between the measured diffraction signal and one of the simulated diffraction signals in the library, the hypothetical profile associated with the simulated diffraction signal is presumed to represent the actual profile of the periodic grating. The hypothetical profiles, which are used to generate the simulated diffraction signals, are generated based on a profile model that characterizes the structure to be examined. Thus, in order to accurately determine the profile of the structure using optical metrology, a profile model that accurately characterizes the structure should be used.

With increased requirement for throughput, decreasing size of the test structures, smaller spot sizes, and lower cost of ownership, there is greater need to optimize design of optical metrology systems to meet several design goals. Characteristics of the optical metrology system including throughput, range of measurement capabilities, accuracy and repeatability of diffraction signal measurements are essential to meeting the increased requirement for smaller spot size and lower cost of ownership of the optical metrology system. Accurate and rapid auto focusing of the workpiece contributes to meeting the above objectives of the optical metrology system.

SUMMARY

Provided is a method for focusing a workpiece in the Z-axis for optical metrology. The auto focusing subsystem includes a focus detector having a tilt angle, a capture range, and a plurality of sensors. A processor coupled to the focus detector is configured to utilize the plurality of focus signals measured using the focus detector to determine two or more focus parameters. The two or more focus parameters and calibration data are used to determine an initial position of the workpiece and to generate instructions to move the workpiece to a best focus position.

BRIEF DESCRIPTION OF DRAWINGS

FIG. 3A depicts an architectural diagram illustrating an auto focusing subsystem of an optical metrology tool whereas

FIG. 5A depicts an exemplary graph of normalized focus signal as a function of workpiece focus position using a calculated first focus parameter $S_P$ whereas

DETAILED DESCRIPTION

In order to facilitate the description of the present invention, a semiconductor wafer may be utilized to illustrate an application of the concept. The systems and processes equally apply to other workpieces that have repeating structures. The workpiece may be a wafer, a substrate, disk, or the like. Furthermore, in this application, the term structure when it is not qualified refers to a patterned structure.

Figure 1:
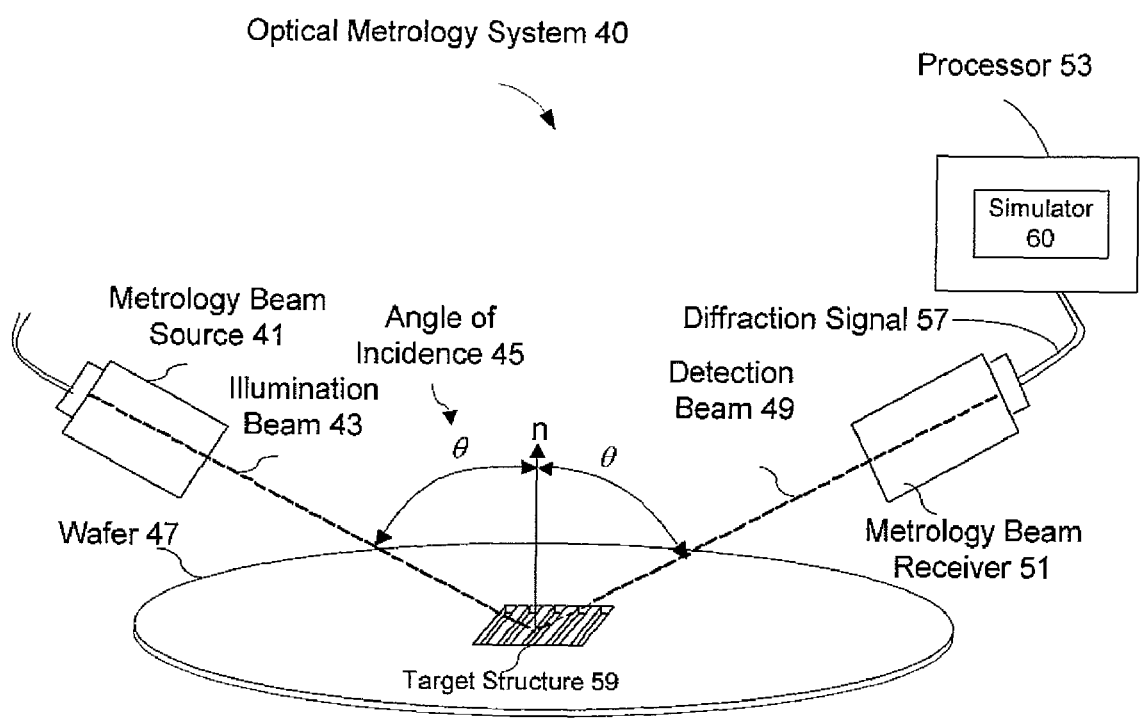
FIG. 1 is an architectural diagram illustrating an exemplary embodiment where an optical metrology system can be utilized to determine the profiles of structures formed on a semiconductor wafer.

FIG. 1 is an architectural diagram illustrating an exemplary embodiment where optical metrology can be utilized to determine the profiles or shapes of structures fabricated on a semiconductor wafer. The optical metrology system 40 includes a metrology beam source 41 projecting a metrology illumination beam 43 at the target structure 59 of a wafer 47. The metrology beam 43 is projected at an incidence angle towards the target structure 59. The diffracted detection beam 49 is measured by a metrology beam receiver 51. A measured diffraction signal 57 is transmitted to a processor 53. The processor 53 compares the measured diffraction signal 57 against a simulator 60 of simulated diffraction signals and associated hypothetical profiles representing varying combinations of critical dimensions of the target structure and resolution. The simulator can be either a library that consists of a machine learning system, pre-generated data base and the like (this is library system), or on demand diffraction signal generator that solves the Maxwell equation for a giving profile (this is regression system). In one exemplary embodiment, the diffraction signal generated by the simulator 60 instance best matching the measured diffraction signal 57 is selected. The hypothetical profile and associated critical dimensions of the selected simulator 60 instance are assumed to correspond to the actual cross-sectional shape and critical dimensions of the features of the target structure 59. The optical metrology system 40 may utilize a reflectometer, an ellipsometer, or other optical metrology device to measure the diffraction beam or signal. An optical metrology system is described in U.S. Pat. No. 6,943,900, entitled GENERATION OF A LIBRARY OF PERIODIC GRATING DIFFRACTION SIGNAL, issued on Sep. 13, 2005, which is incorporated herein by reference in its entirety.

Simulated diffraction signals can be generated by applying Maxwell's equations and using a numerical analysis technique to solve Maxwell's equations. It should be noted that various numerical analysis techniques, including variations of RCWA, can be used. For a more detail description of RCWA, see U.S. Pat. No. 6,891,626, titled CACHING OF INTRA-LAYER CALCULATIONS FOR RAPID RIGOROUS COUPLED-WAVE ANALYSES, filed on Jan. 25, 2001, issued May 10, 2005, which is incorporated herein by reference in its entirety.

Simulated diffraction signals can also be generated using a machine learning system (MLS). Prior to generating the simulated diffraction signals, the MLS is trained using known input and output data. In one exemplary embodiment, simulated diffraction signals can be generated using an MLS employing a machine learning algorithm, such as back-propagation, radial basis function, support vector, kernel regression, and the like. For a more detailed description of machine learning systems and algorithms, see U.S. Pat. No. 7,831,528 issued on Nov. 9, 2010, titled OPTICAL METROLOGY OF STRUCTURES FORMED ON SEMICONDUCTOR WAFERS USING MACHINE LEARNING SYSTEMS, a continuation of U.S. patent application Ser. No. 10/608,300 filed on Jun. 27, 2003, which is incorporated herein by reference in its entirety.

Figure 2:
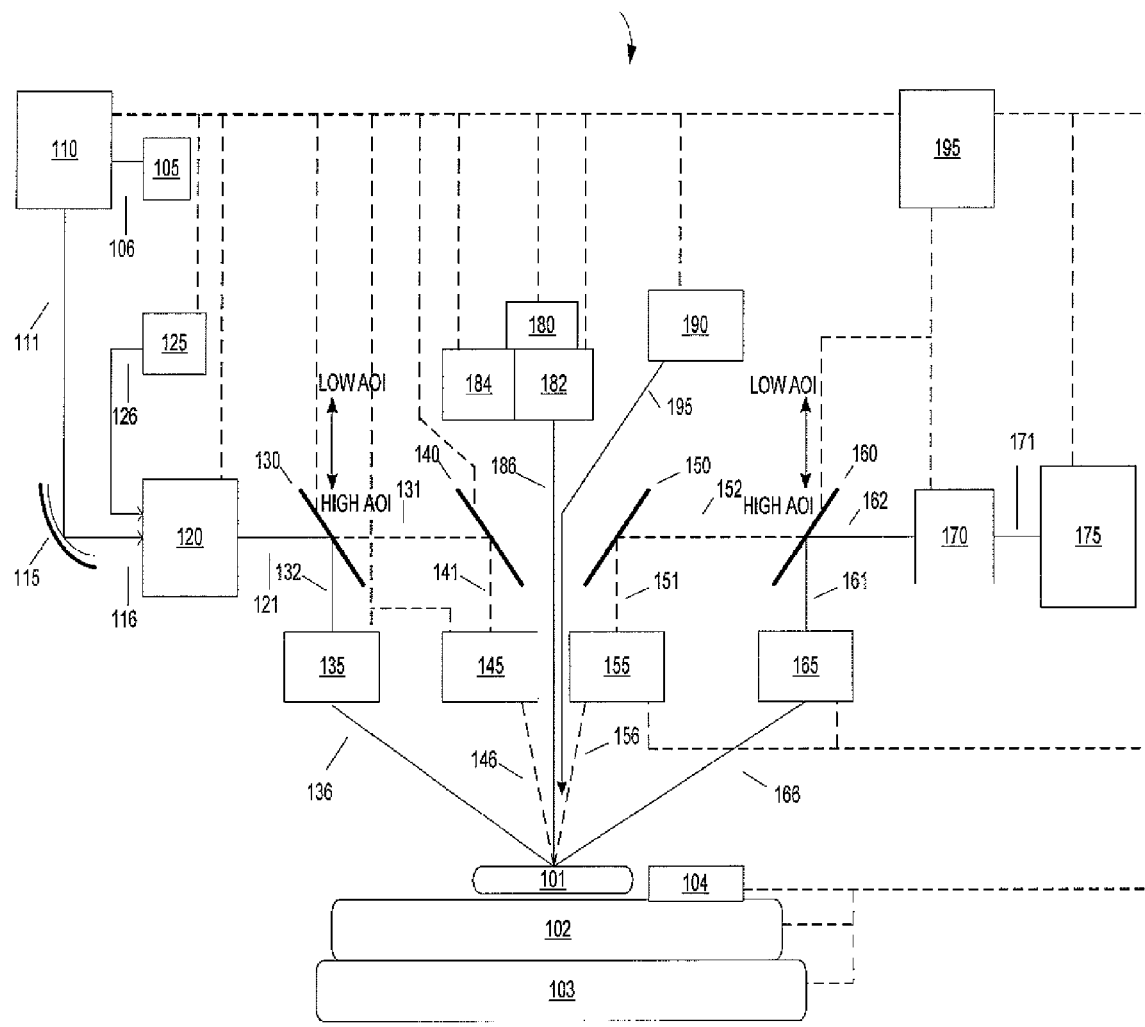
FIG. 2 depicts an exemplary optical metrology system in accordance with embodiments of the invention.

FIG. 2 shows an exemplary block diagram of an optical metrology system in accordance with embodiments of the invention. In the illustrated embodiment, an optical metrology system 100 can comprise a lamp subsystem 105, and at least two optical outputs 106 from the lamp subsystem can be transmitted to an illuminator subsystem 110. At least two optical outputs 111 from the illuminator subsystem 110 can be transmitted to a selector subsystem 115. The selector subsystem 115 can send at least two signals 116 to a beam generator subsystem 120. In addition, a reference subsystem 125 can be used to provide at least two reference outputs 126 to the beam generator subsystem 120. The wafer 101 is positioned using an X-Y-Z-theta stage 102 where the wafer 101 is adjacent to a wafer alignment sensor 104, supported by a platform base 103.

The optical metrology system 100 can comprise a first selectable reflection subsystem 130 that can be used to direct at least two outputs 121 from the beam generator subsystem 120 on a first path 131 when operating in a first mode "LOW Angle of Incidence (AOI)" or on a second path 132 when operating in a second mode "HIGH AOI". When the first selectable reflection subsystem 130 is operating in the first mode "LOW AOI", at least two of the outputs 121 from the beam generator subsystem 120 can be directed to a first reflection subsystem 140 as outputs 131, and at least two outputs 141 from the first reflection subsystem can be directed to a high angle focusing subsystem 145. When the first selectable reflection subsystem 130 is operating in the second mode "HIGH AOI", at least two of the outputs 121 from the beam generator subsystem 120 can be directed to a low angle focusing subsystem 135 as outputs 132. Alternatively, other modes in addition to "LOW AOI" and "HIGH AOI" may be used and other configurations may be used.

When the metrology system 100 is operating in the first mode "LOW AOI", at least two of the outputs 146 from the high angle focusing subsystem 145 can be directed to the wafer 101. For example, a high angle of incidence can be used. When the metrology system 100 is operating in the second mode "HIGH AOI", at least two of the outputs 136 from the low angle focusing subsystem 135 can be directed to the wafer 101. For example, a low angle of incidence can be used. Alternatively, other modes may be used and other configurations may be used.

The optical metrology system 100 can comprise a high angle collection subsystem 155, a low angle collection subsystem 165, a second reflection subsystem 150, and a second selectable reflection subsystem 160.

When the metrology system 100 is operating in the first mode "LOW AOI", at least two of the outputs 156 from the wafer 101 can be directed to the high angle collection subsystem 155. For example, a high angle of incidence can be used. In addition, the high angle collection subsystem 155 can process the outputs 156 obtained from the wafer 101 and high angle collection subsystem 155 can provide outputs 151 to the second reflection subsystem 150, and the second reflection subsystem 150 can provide outputs 152 to the second selectable reflection subsystem 160. When the second selectable reflection subsystem 160 is operating in the first mode "LOW AOI" the outputs 152 from the second reflection subsystem 150 can be directed to the analyzer subsystem 170. For example, at least two blocking elements can be moved allowing the outputs 152 from the second reflection subsystem 150 to pass through the second selectable reflection subsystem 160 with a minimum amount of loss.

When the metrology system 100 is operating in the second mode "HIGH AOI", at least two of the outputs 166 from the wafer 101 can be directed to the low angle collection subsystem 165. For example, a low angle of incidence can be used. In addition, the low angle collection subsystem 165 can process the outputs 166 obtained from the wafer 101 and low angle collection subsystem 165 can provide outputs 161 to the second selectable reflection subsystem 160. When the second selectable reflection subsystem 160 is operating in the second mode "HIGH AOI" the outputs 162 from the second selectable reflection subsystem 160 can be directed to the analyzer subsystem 170.

When the metrology system 100 is operating in the first mode "LOW AOI", high incident angle data from the wafer 101 can be analyzed using the analyzer subsystem 170, and when the metrology system 100 is operating in the second mode "HIGH AOI", low incident angle data from the wafer 101 can be analyzed using the analyzer subsystem 170.

Metrology system 100 can include at least two measurement subsystems 175. At least two of the measurement subsystems 175 can include at least two detectors such as spectrometers. For example, the spectrometers can operate from the Deep-Ultra-Violet to the visible regions of the spectrum.

The metrology system 100 can include at least two camera subsystems 180, at least two illumination and imaging subsystems 182 coupled to at least two of the camera subsystems 180. In addition, the metrology system 100 can also include at least two illuminator subsystems 184 that can be coupled to at least two of the imaging subsystems 182.

In some embodiments, the metrology system 100 can include at least two auto-focusing subsystems 190. Alternatively, other focusing techniques may be used.

At least two of the controllers (not shown) in at least two of the subsystems (105, 110, 115, 120, 125, 130, 135, 140, 145, 150, 155, 160, 165, 170, 175, 180, 182, 190, and 195) can be used when performing measurements of the structures. A controller can receive real-signal data to update subsystem, processing element, process, recipe, profile, image, pattern, and/or model data. At least two of the subsystems (105, 110, 115, 120, 125, 130, 135, 140, 145, 150, 155, 160, 165, 170, 175, 180, 182, and 190) can exchange data using at least two Semiconductor Equipment Communications Standard (SECS) messages, can read and/or remove information, can feed forward, and/or can feedback the information, and/or can send information as a SECS message.

Those skilled in the art will recognize that at least two of the subsystems (105, 110, 115, 120, 125, 130, 135, 140, 145, 150, 155, 160, 165, 170, 175, 180, 182, 190, and 195) can include computers and memory components (not shown) as required. For example, the memory components (not shown) can be used for storing information and instructions to be executed by computers (not shown) and may be used for storing temporary variables or other intermediate information during the execution of instructions by the various computers/processors in the metrology system 100. At least two of the subsystems (105, 110, 115, 120, 125, 130, 135, 140, 145, 150, 155, 160, 165, 170, 175, 180, 185, and 190) can include the means for reading data and/or instructions from a computer readable medium and can comprise the means for writing data and/or instructions to a computer readable medium. The metrology system 100 can perform a portion of or all of the processing steps of the invention in response to the computers/processors in the processing system executing at least two sequences of at least two instructions contained in a memory and/or received in a message. Such instructions may be received from another computer, a computer readable medium, or a network connection. In addition, at least two of the subsystems (105, 110, 115, 120, 125, 130, 135, 140, 145, 150, 155, 160, 165, 170, 175, 180, 182, and 190) can comprise control applications, Graphical User Interface (GUI) components, and/or database components.

It should be noted that the beam when the metrology system 100 is operating in the first mode "LOW AOI" with a high incident angle data from the wafer 101 all the way to the measurement subsystems 175, (output 166, 161, 162, and 171) and when the metrology system 100 is operating in the second mode "HIGH AOI" with a low incident angle data from the wafer 101 all the way to the measurement subsystems 175, (output 156, 151, 152, 162, and 171) is referred to as diffraction signal(s).

The present invention is an auto focus subsystem that can be applied to any microscope-based system that views or measures reflective workpieces. The auto focus subsystem is particularly useful for small-spot metrology instruments such as reflectometers, scatterometers and ellipsometers where very precise focusing is needed to obtain accurate measurements, where the focusing must be done quickly in a production environment, and where focusing measurements use a relatively large capture range. Existing auto focus systems in microscopes use numerous techniques. Among the many general auto focus system types are those that can be called off-axis designs. In these designs, a beam is incident at an angle to the workpiece. The reflected light is then projected onto a detector that measures the position of a spot formed from the reflected beam. The position of the spot indicates the height of the workpiece. A method of calibration is then used to correlate workpiece height to spot position. The correlation of workpiece height to spot position is used to find a particular spot position on the detector corresponding to best focus.

Figure 3A:
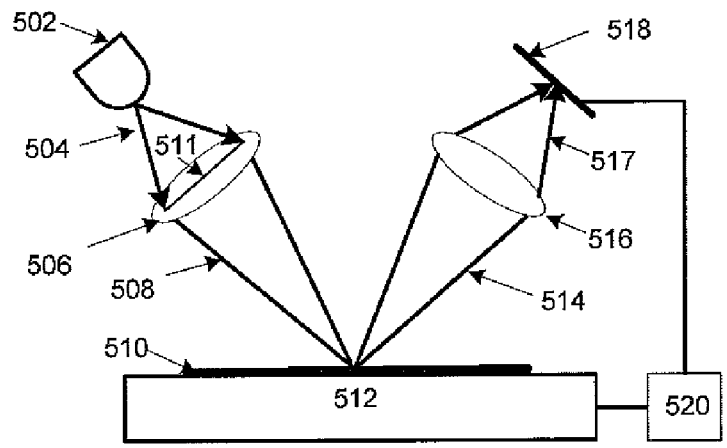

FIG. 3A depicts an architectural diagram illustrating an auto focusing subsystem of an optical metrology tool. Referring to FIG. 3A, the auto focusing subsystem of an optical metrology tool 500 comprises a focus illumination source 502 generating a focus illumination beam 504 directed to optical focusing component 506 further generating focus projection beam 508 onto a workpiece 510. The focusing illumination source 502 is point-like source which could have one of several configurations such an LED behind a pinhole or a laser with diverging optics. The focusing illumination beam 504 is collected by lens 506 which focuses an illumination beam image 511 of the source and transmitted as focus projection beam 508 onto the workpiece 510. In other embodiments, the lens 504 may be a plurality of mirrors or may comprise a combination of mirrors or lenses. As mentioned above, the workpiece 510 may be a wafer, a photomask, substrate or the like. The workpiece 510 is coupled to a motion control subsystem 512 that may be an X-Y-Z theta stage. Reflected light 514 is diffracted off the workpiece and collected by lens 516 and is focused to form another image of the source spot onto the focus detector 518. In other embodiments, the lens 516 may be a plurality of mirrors or may comprise a combination of mirrors or lenses. The focus detector 518 produces a signal that is processed and interpreted by the collection electronics and processor 520 to determine the position of the spot and height of the workpiece 510 on the Z-axis. Based on this determined height of the workpiece 510 and previously calibrated best focus position, the processor 520 sends instructions to the motion control subsystem 512 to move the workpiece 510 to the best focus position on the Z-axis. Typically, the microscope optics (not shown) for viewing and measuring the workpiece 510 would be located between the two lenses 506 and 516.

Figure 3B:
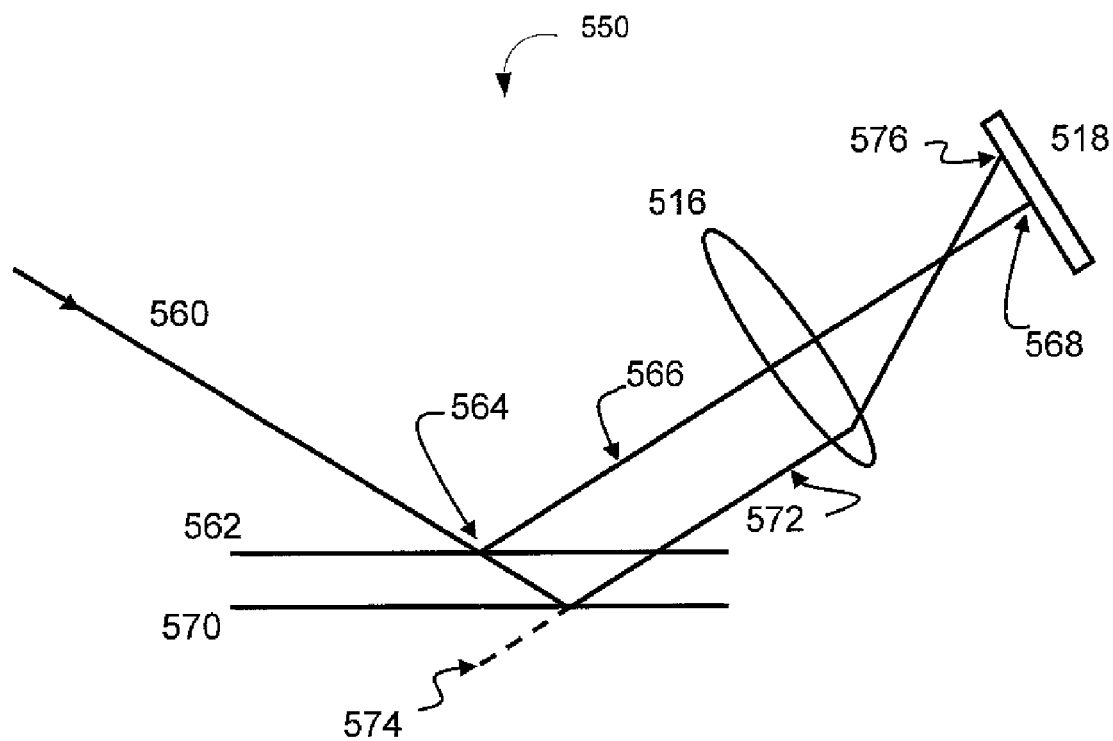
FIG. 3B depicts an architectural diagram illustrating diffraction of an auto focus beam off a workpiece at different positions on the Z-axis.

FIG. 3B depicts an architectural diagram illustrating diffraction of an auto focus beam off a workpiece at different positions on the Z-axis. FIG. 3B shows the chief rays with different workpiece heights to illustrate why the workpiece height affects the position on the detector 518. The incident chief ray 560 is incident on the workpiece at best focus position 562 at point 564. The reflected chief ray 566 is focused by lens 516 onto detector 518 at point 568. However with the workpiece at position 570, the reflected chief ray is now shifted, 572, so that it appears to originate from point 574 and is now focused onto detector 518 at point 576.

The prior art system of FIG. 3A can have many variations. If the light source is narrow and nearly collimated, such as a laser, the lenses can be eliminated entirely, although there is a reduction in focus sensitivity and an undesired increase in sensitivity to workpiece tilt. Having no lenses produces a larger spot that is often not as accurate as required on a patterned workpiece. Also, instead of employing two lenses, the incident and reflected beams could be collected by the outer portions of an aperture of a single large numerical aperture (NA) objective. Such an objective may be a reflective objective such as a Schwarzchild objective or related designs. Having separate lenses for auto focus such as 506 and 516 in FIG. 3A may be useful when the main microscope objective (not shown) is already used to focus multiple beams for metrology purposes. The optical path will also typically have adjustments (not shown) to optimize the position of the focused spot on the workpiece 510 and on the detector 518.

The detector 518 in FIG. 3A and FIG. 3B is typically one of three types: a position sensitive detector (PSD), a linear diode array (LDA), or a quadrant (or bi-cell) photodiode. A PSD is capable of sensing a large range of motion (depending on the optical magnification), but it is then not as sensitive as the LDA or quadrant detector to small movements. The quadrant detector has small useful range that is only equal to less than twice the width of the spot it is sensing, but it is very sensitive to movements of the workpiece. The LDA has good range and sensitivity to movements of the workpiece, but is potentially slower and more expensive as it requires firmware and more complicated electronics.

Figure 4A:
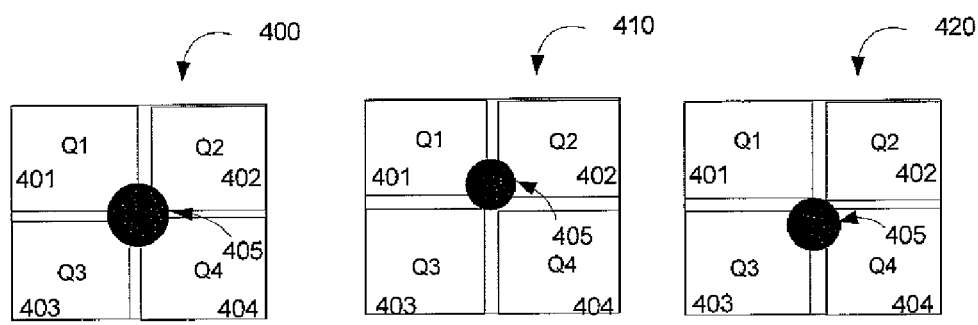
FIG. 4A depicts three auto focusing quadrant detectors, a first detector with the focus detection beam in the center, a second detector with the focus detection beam at a maximum range above center, and a third detector with the focus detection beam at a maximum range below center of the detector.

FIG. 4A shows how a quadrant detector would be used in a prior art system to find the position of the spot, 405, focused onto it. (It is also possible to use a bi-cell detector with the gap between the two cells horizontal.) FIG. 4A, diagram 400 shows the spot nearly centered on the quadrant detector as it would be with the workpiece at best focus. (In practice the spot is not perfectly centered at best focus, but this position is calibrated.) Q1, Q2, Q3, and Q4 are the signals generated by the corresponding four quadrants 401, 402, 403, and 404. Each quadrant acts like an independent photodiode with a small gap in between adjacent quadrants.

The process of focusing optics to a target may be characterized with focus parameters. A focus parameter may be used to express relationship of focus signals, corresponding location of the workpiece on the Z-axis, current position relative to the best focus location, tilt angle of the focus detector, focus beam spot position relative to the one or more sensors, or combinations of the foregoing. In one embodiment, one or more focus parameters may express the distance or proximity to the best focus location as a function of focus signals from one or more sensors of the focus detector. In another embodiment, a focus parameter may express the ratio of focus signal measurement from one or more sensors compared to the total of focus signal measurements of all the sensors of the focus detector.

In the example of a quadrant detector depicted in FIG. 4A, two or more focus parameters can be formulated to use focus signals Q1, Q2, Q3, and Q4 that indicates how the focus signal varies with the position of workpiece in the Z-axis. Two focus parameters $S_P$ and $S_R$ are described in detail to illustrate the concepts of the invention. The first focus parameter, $S_P$, is derived by calculating the difference of the sum of focus signal in the upper quadrants, 401 and 402, and the sum of focus signals in lower quadrants, 403 and 404, divided by the total of the focus signals in all the quadrants as shown in the following equation:

$$S_P = \frac{(Q1 + Q2) - (Q3 + Q4)}{Q1 + Q2 + Q3 + Q4}. \qquad 1.1.1$$

Figure 5A:
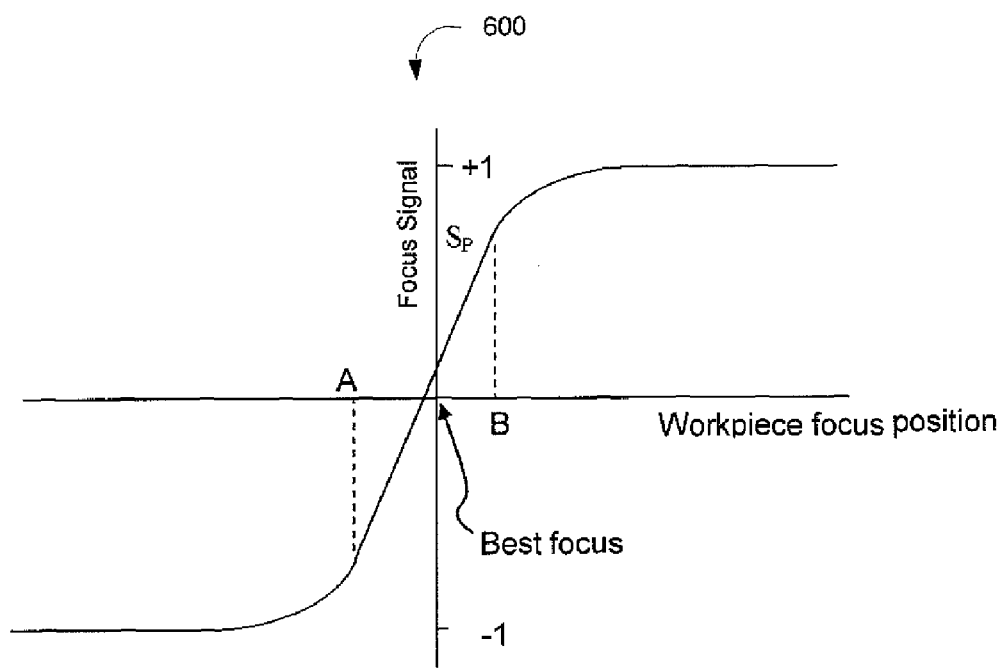

With reference to FIG. 5A, $S_P$ is linear or substantially linear with respect to spot position 405 and workpiece height only over a small range. For the rest of the specifications, the phrase linear range shall mean linear or substantially linear range. Referring to FIG. 4A, diagrams 410 and 420 show the spot position 405 when it has moved to the end of the linear range. When the spot position 405 moves beyond these positions, there is no light falling on either the top two quadrants 401 and 402 or the bottom two quadrants 403 and 404. Information on the exact position of the spot 405 is lost. The only information available is that the position of the spot 405 is in either the upper half or lower half.

A plot of $S_P$ versus workpiece height is shown in FIG. 5A. When the workpiece is between positions A and B, the signal is particularly useful in controlling the motion control system or Z stage to rapidly move the workpiece to the best focus position. The range of focus parameter values, such as between positions A and B in FIG. 5A, is referred to as the capture range. Since the slope of the curve between A and B has been previously calibrated, the processor can calculate $S_P$ and then determine the Z move needed to put the workpiece near best focus. For very accurate focusing, a second iterative step may be needed. Alternatively, the focus parameter could be used as the error signal in a servo loop driving the motion control system or Z stage motor. However, if the workpiece starts out below A or above B, then the processor does not have good information on how far to move the Z stage or direct the motion control system and many more steps are needed, taking more time. The lack of a large capture range is a large drawback to using a quadrant detector. A large advantage, though, is that the linear range of the signal is very steep, causing a small change in focus position to cause a relatively large change in signal.

Figure 4B:
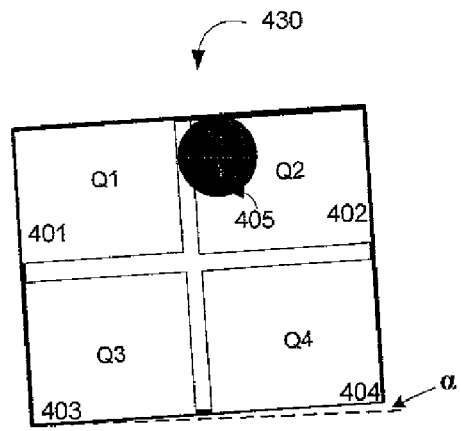
FIG. 4B depicts an auto focusing quadrant detector with a tilt angle and with the focus detector beam off center to the top right sensor.
Figure 4C:
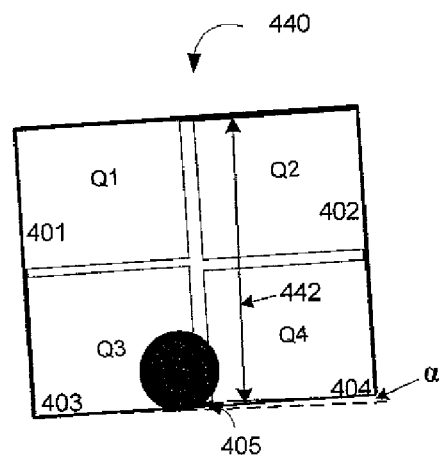
FIG. 4C depicts an auto focusing quadrant detector with the focus detector beam off center to the bottom left sensor.

The present invention takes advantage of the simplicity and high sensitivity of the quadrant detector while also increasing the linear capture range. In the present invention, the quadrant detector is rotated by a small angle α as shown in FIGS. 4B and 4C. This angle is chosen so that when the spot, 405, has reached the top edge of the detector, as shown in FIG. 4B, or the bottom, as shown in FIG. 4C, the spot also has shifted off either the left or right half of the detector. The second focus parameter, $S_R$, determines the difference of the sum of focus signals detected on the left half quadrants, 401 and 403, and the sum of focus signals detected on the right half quadrants, 402 and 404, divided by the total of all the focus signal in all the quadrants as shown in the following equation:

$$S_R = \frac{(Q1 + Q3) - (Q2 + Q4)}{Q1 + Q2 + Q3 + Q4} \qquad 1.1.2$$

Figure 5B:
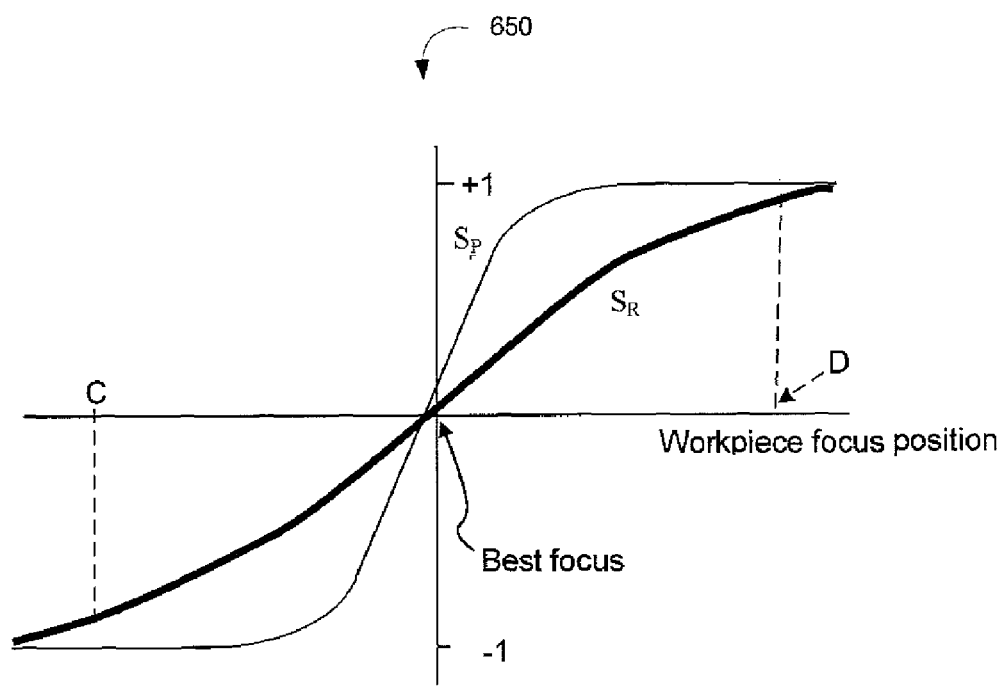
FIG. 5B depicts an exemplary graph of normalized focus signal as a function of workpiece focus position using a calculated first and second focus parameters $S_P$ and $S_R$.

A plot of $S_R$ and $S_P$ is shown in FIG. 5B. The plot of focus parameter $S_R$ is not as steep as $S_P$, but $S_R$ has a larger linear capture range that can be used as a coarse focus signal that can quickly be used to bring the workpiece height into the range where $S_P$ can then be used as a fine focus signal. In practice the ratio of the slopes and capture ranges between the two focus parameters can be as much as 30:1. It is understood that other focus parameters including one that takes into account the tilt angle and other configurations of the sensors of the focus detector can be formulated and used to control auto focusing movement of the workpiece to the best focus position.

Figure 6:
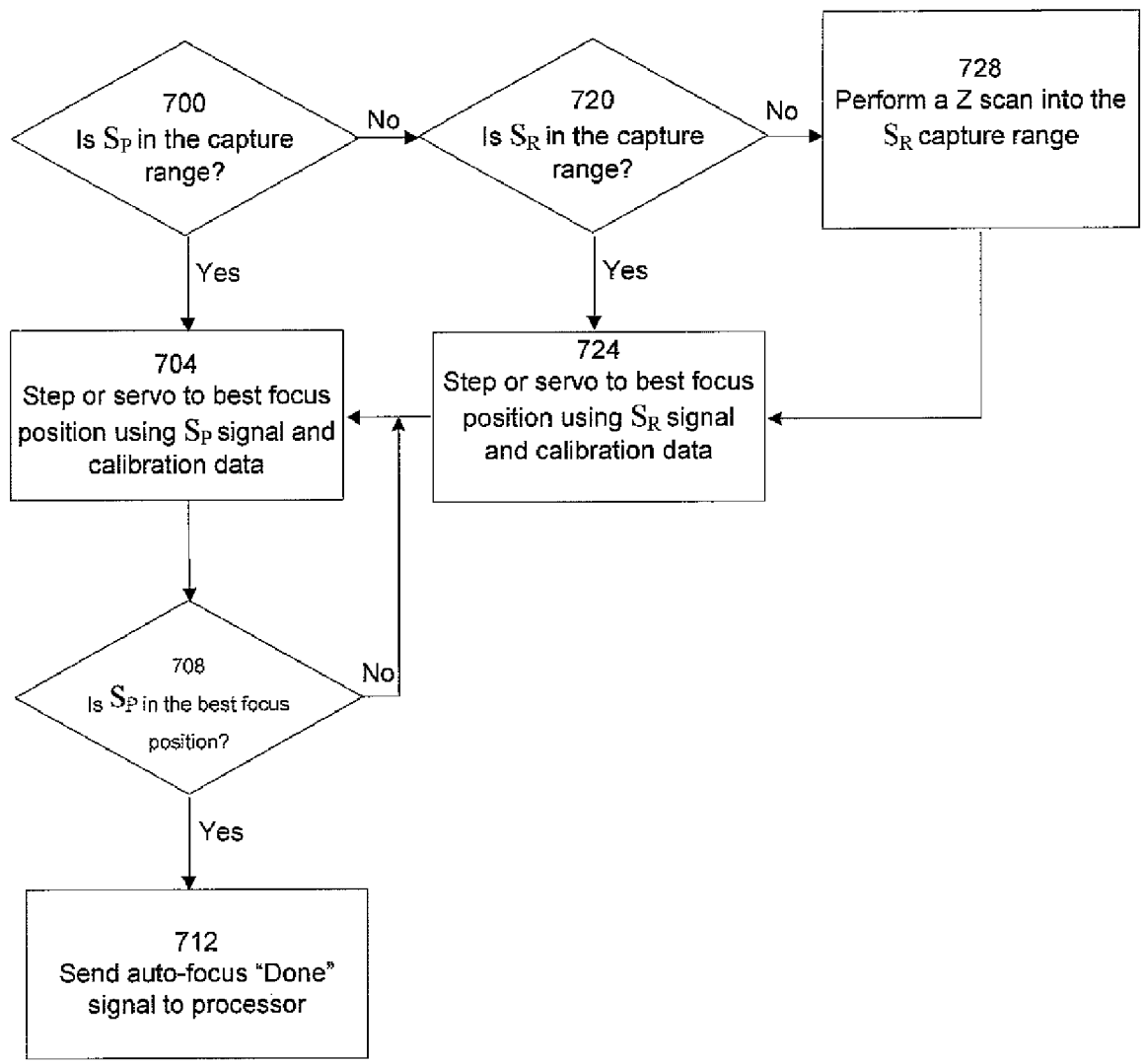
FIG. 6 depicts an exemplary flowchart for auto focusing the workpiece in the Z-axis using a quadrant detector and calculated first and second focus parameters $S_P$ and $S_R$.

FIG. 6 depicts an exemplary flowchart for auto focusing the workpiece in the Z-axis using a quadrant detector and calculated first and second focus parameters $S_P$ and $S_R$ of the present invention. In step 700, value of the focus parameter, $S_P$, for example, calculated using Equation 1.1.1, and compared to the linear range of the workpiece focus position versus the focus signal graph in FIG. 5A, the linear or substantially linear range delineated as the area bounded by A and B area in the graph. If $S_P$ is within the linear range, then in step 704, the $S_P$ and the calibration data previously obtained for the focus detector are used to step or servo the motion control system or Z-stage to the best focus position in the Z-axis. The best focus position is determined by using the calibration of the focus detector and noting the height or Z-position of a workpiece when the $S_P$ is closest to zero. In step 708, if $S_P$ is in the best focus position, that is, the $S_P$ value is closest to the $S_P$ value determined in the calibration process as the best focus position, an auto focus "Done" signal is sent to the processor, step 712. The processor may be the processor 520 in FIG. 3A. Alternatively, the processor may be a processor in the optical metrology system or a processor in the fabrication cluster or any processor accessible to the focus detector. If the $S_P$ is not in the best focus position, steps 704 and 708 are iterated until the best focus position of the workpiece is achieved.

Referring to FIG. 6, if the $S_P$ is not in the linear range of the focus detector as determined in step 700, a rough position of the focus detector spot may be determined, for example, by using Equation 1.1.2. As mentioned above, $S_R$ is calculated by comparing the focus signals detected on the left half compared to the right half of the focus detector. In step 720, the calculated value of $S_R$ is compared to the range of values within the linear range, such as the area bounded by C and D in FIG. 5B, an area where the graph of focus signal to workpiece position shows the curve is relatively linear. If $S_R$ is within the linear range, then in step 724, $S_R$ and the calibration data previously obtained for the focus detector is used to step or servo the motion control system or Z-stage to the best focus position. Once the best focus position if obtained using $S_R$, processing proceeds to step 704 where $S_P$ and the calibration data previously obtained for the focus detector are used to step or servo the motion control system or Z-stage to the best focus position. Processing proceeds to step 708 and to step 712 if best focus position is achieved or iterates to steps 704 and 708 until the best focus position of the workpiece is achieved using $S_P$.

Still referring to FIG. 6, if the calculated $S_R$ is not in the linear range, then a scan into the $S_R$ linear range is performed. This is typically done by performing a slow scan where the workpiece is moved up or down until the determined $S_R$ is within the linear range, for example, the area bounded by C and D in FIG. 5B. Once the calculated $S_R$ is within the linear range, then processing proceeds to step 724. Once the best focus position if obtained using $S_R$, processing proceeds to step 704 where $S_P$ and the calibration data previously obtained for the focus detector is used to step or servo the motion control system or Z-stage to the best focus position. Similar to the method above, processing proceeds to step 708 and to step 712 if best focus position is achieved or iterates to steps 704 and 708 until the best focus position of the workpiece is achieved using $S_P$.

Referring to FIG. 6, a motion control subsystem, a three-dimensional stage, or Z-stage can be used to move the workpiece to the best focus position, utilizing a processor. As mentioned above, a processor of the motion control subsystem or stage or some other processor as illustrated in the description for FIG. 5A and/or FIG. 2 may be used to transmit and control the movement of the workpiece to the best focus position. Although the description of the method in FIG. 6 specified the focus parameters being in the linear range or substantially linear range, other non-linear ranges may be utilized as long as a correlation of the focus parameter can be expressed in a function or mathematical algorithm. Correlation may be developed using calibration data comprising focus signal and workpiece position on the Z-axis through the use statistical or mathematical curve fitting methods. Curve fitting methods such as polynomials, least squares, or nonlinear regression algorithms and software packages using Table Curve™, Matlab™, Fityk™, and the like, which are generally known to people in the art, may be used to develop the correlation for focus signals and workpiece position.

Figure 7:
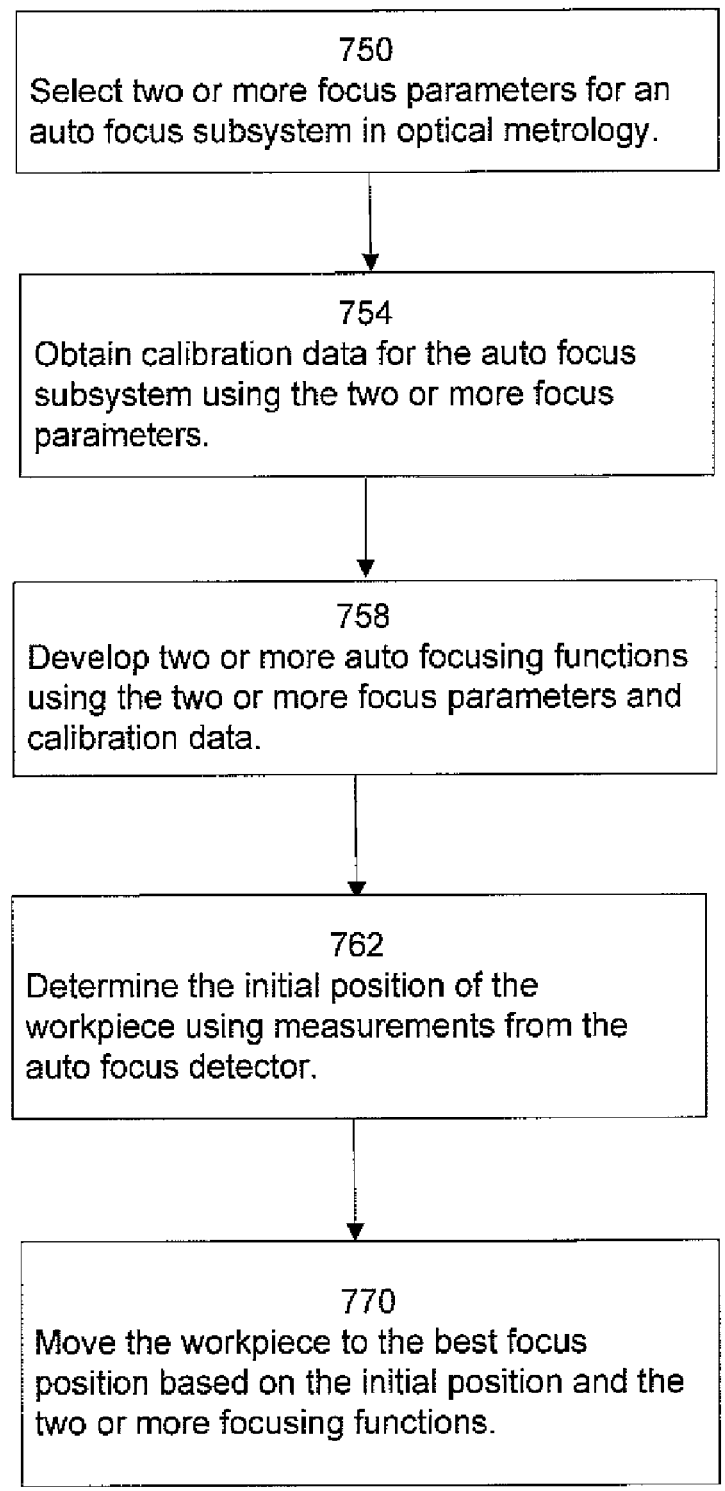
FIG. 7 depicts an exemplary flowchart for auto focusing a workpiece for optical metrology in one embodiment of the invention.

FIG. 7 depicts an exemplary flowchart for auto focusing a workpiece for optical metrology in one embodiment of the invention. In step 750, two or more focus parameters for the auto focus subsystem are selected. $S_P$ as expressed in Equation 1.1.1 and $S_R$ as expressed in Equation 1.1.2 may be selected as the two or more focus parameters for the auto focus subsystem. In step 754, calibration data for the auto focus subsystem may be obtained using the selected two or more focus parameters. As described above, other focus parameters such tilt angle and other configurations of the sensors of the focus detector can be formulated and used to control auto focusing movement of the workpiece to the best focus position. Continuing with the quadrant detector example above, data on the focus signal measurements at various Z-axis positions are collected. $S_P$ and $S_R$ values are calculated and the corresponding Z-axis positions can be stored in a lookup table, database, spreadsheet file or graph. In step 758, two or more focusing functions using the two or more focus parameters are developed. The functions may comprise a lookup table, a graph or curve of normalized $S_P$ and $S_R$ values as function of workpiece focus position as depicted in FIG. 5A and FIG. 5B, a database of the same set of data values, or equations such as Equations 1.1.1 and 1.1.2 or the like.

Still referring to FIG. 7, in step 762, the initial position of the workpiece is determined using focus signal measurements using the focus detector and the two or more focusing functions developed in step 758. Again using the previous example of a quadrant detector, focus signal measurements of the four quadrants are obtained and the normalized $S_P$ and $S_R$ values are calculated. Using the focusing functions such as a graph or a lookup table or equation described above, the initial workpiece position on the Z-axis is determined. In step 770, the workpiece is moved to the best focus position using the initial workpiece position and the two or more focusing functions. As an example, the workpiece may be moved to the best focus position using the method described in relation to FIG. 6. A processor such as the processor 520 depicted in FIG. 3A or other processor in the auto focusing subsystem or the optical metrology system FIG. 2 may be used to control moving the workpiece to the best focus position. As can be seen in the FIGS. 5A and 5B, the best focus position is close to the Z-axis position where the focus parameters $S_P$ and $S_R$ values are zero or substantially zero.

Figure 8:
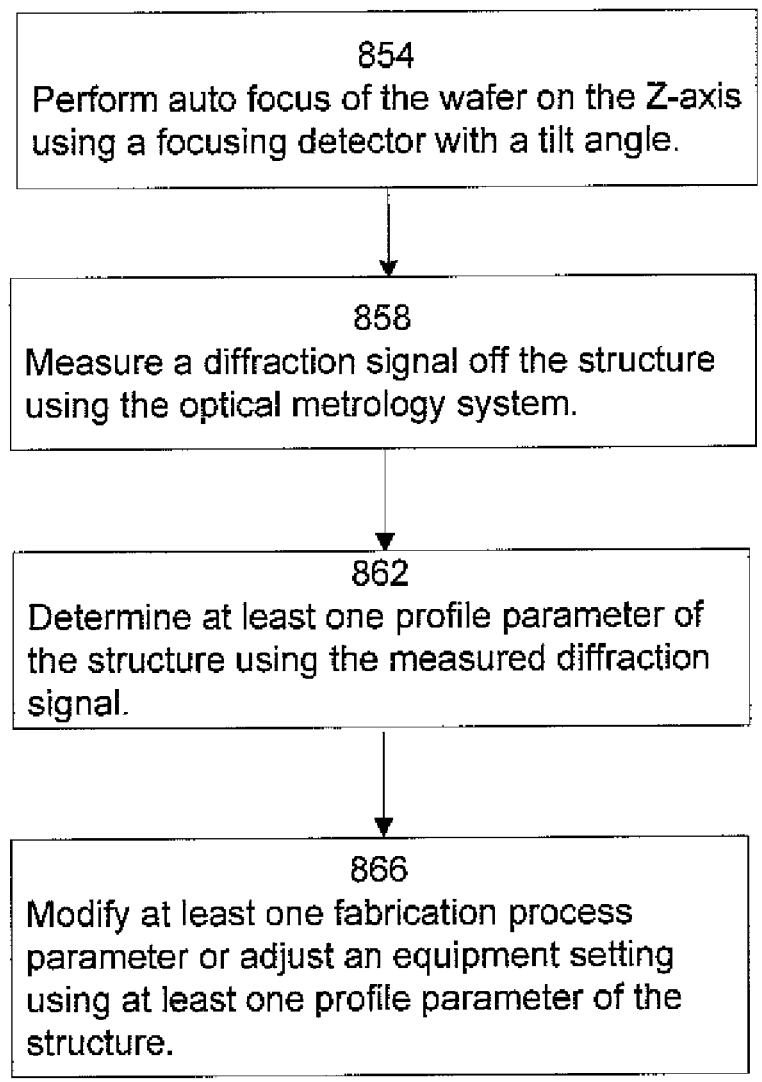
FIG. 8 depicts an exemplary flowchart for auto focusing a workpiece for optical metrology measurements of a structure on the workpiece, extracting structure profile parameters and controlling a fabrication process in one embodiment of the invention.

FIG. 8 depicts an exemplary flowchart for using an optical metrology system to extract structure profile parameters and control a fabrication process in one embodiment of the invention. In step 854, auto focus of a workpiece is performed using a focus detector with a tilt angle. The steps of performing the auto focus are the process steps described in relation to FIG. 6 or FIG. 7. In step 858 of FIG. 8, one or more diffraction signals off a target structure on the workpiece are measured with an optical metrology system, using the workpiece focused on the Z-axis in step 854. In step 862, at least one profile parameter of the structure is determined using the measured one or more diffraction signals. If the workpiece is a semiconductor wafer, the one profile parameter may be a top critical dimension (CD), a bottom CD, or a sidewall angle. In step 866, at least one fabrication process parameter or equipment setting is modified using the determined at least one profile parameter of the structure. For example, if the workpiece is a wafer, the fabrication process parameter may include a temperature, exposure dose or focus, etchant concentration or gas flow rate. As mentioned above, the optical metrology system may be part of a standalone metrology module or integrated in a fabrication cluster.

Figure 9:
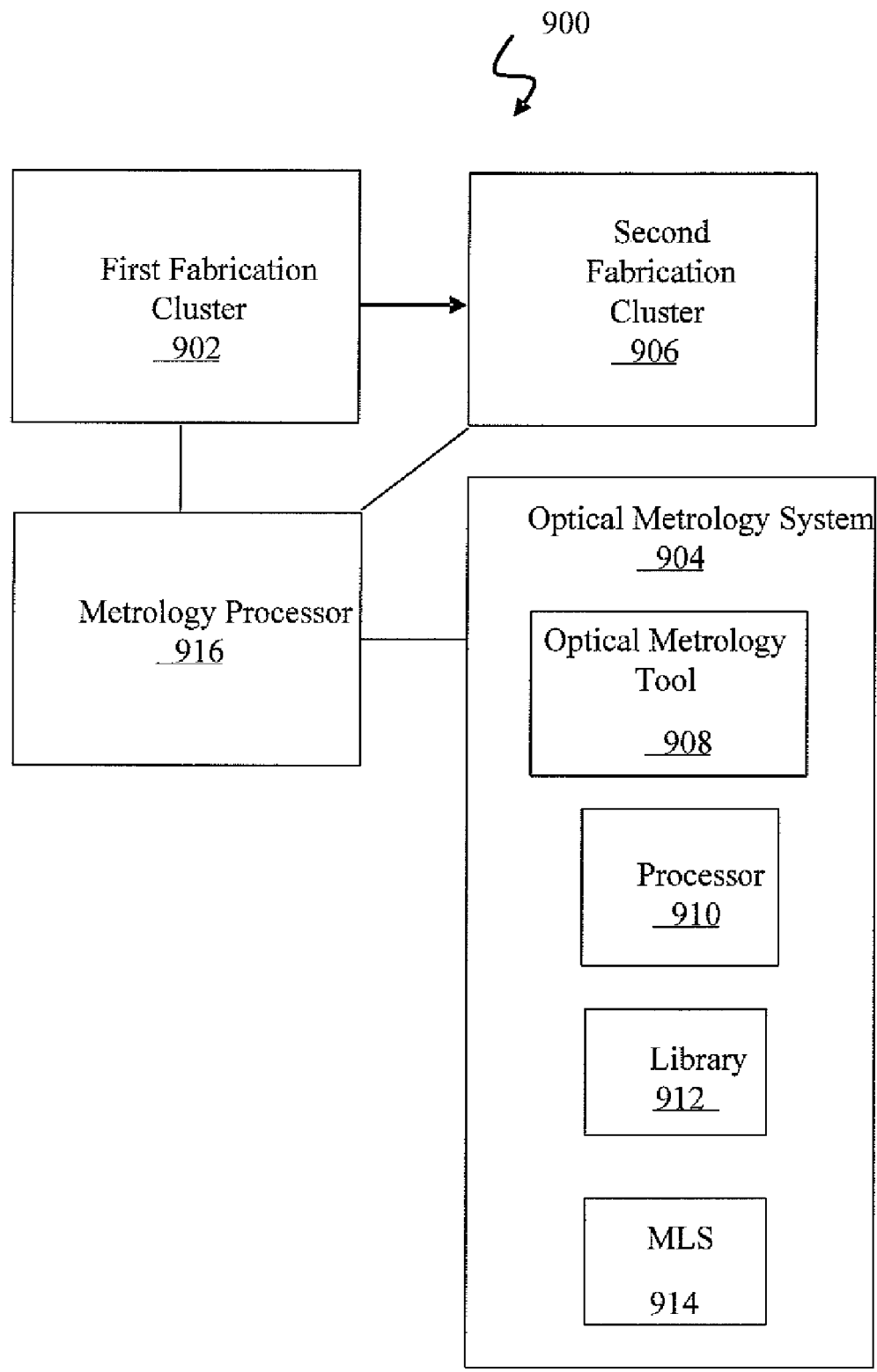
FIG. 9 is an exemplary block diagram of a system for determining and utilizing profile parameters for automated process and equipment control.

FIG. 9 is an exemplary block diagram of a system for determining and utilizing profile parameters for automated process and equipment control. System 900 includes a first fabrication cluster 902 and optical metrology system 904. System 900 also includes a second fabrication cluster 906. Although the second fabrication cluster 906 is depicted in FIG. 9 as being subsequent to first fabrication cluster 902, it should be recognized that second fabrication cluster 906 can be located prior to first fabrication cluster 902 in system 900 (e.g. and in the manufacturing process flow).

A photolithographic process, such as exposing and/or developing a photoresist layer applied to a wafer, can be performed using first fabrication cluster 902. Optical metrology system 904 is similar to optical metrology system 40 of FIG. 1. In one exemplary embodiment, optical metrology system 904 includes an optical metrology tool 908 and processor 910. Optical metrology tool 908 is configured to measure a diffraction signal off of the structure. Processor 910 is configured to compare the measured diffraction signal measured by the optical metrology tool designed to meet plurality of design goals to a simulated diffraction signal. As mentioned above, the simulated diffraction is determined using a set of profile parameters of the structure and numerical analysis based on the Maxwell equations of electromagnetic diffraction. In one exemplary embodiment, optical metrology system 904 can also include a library 912 with a plurality of simulated diffraction signals and a plurality of values of one or more profile parameters associated with the plurality of simulated diffraction signals. As described above, the library can be generated in advance; metrology processor 910 can compare a measured diffraction signal off a structure to the plurality of simulated diffraction signals in the library. When a matching simulated diffraction signal is found, the one or more values of the profile parameters associated with the matching simulated diffraction signal in the library is assumed to be the one or more values of the profile parameters used in the wafer application to fabricate the structure.

System 900 also includes a metrology processor 916. In one exemplary embodiment, processor 910 can transmit the one or more values of the one or more profile parameters to metrology processor 916. Metrology processor 916 can then adjust one or more process parameters or equipment settings of the first fabrication cluster 902 based on the one or more values of the one or more profile parameters determined using optical metrology system 904. Metrology processor 916 can also adjust one or more process parameters or equipment settings of the second fabrication cluster 906 based on the one or more values of the one or more profile parameters determined using optical metrology system 904. As noted above, second fabrication cluster 906 can process the wafer before or after first fabrication cluster 902. In another exemplary embodiment, processor 910 is configured to train machine learning system 914 using the set of measured diffraction signals as inputs to machine learning system 914 and profile parameters as the expected outputs of machine learning system 914.

Although exemplary embodiments have been described, various modifications can be made without departing from the spirit and/or scope of the present invention. For example, although a quadrant detector was primarily used to describe the embodiments of the invention; other position sensitive detectors may also be used. For automated process control, the fabrication clusters may be a track, etch, deposition, chemical-mechanical polishing, thermal, or cleaning fabrication cluster. Furthermore, the elements required for the auto focusing are substantially the same regardless of whether the optical metrology system is integrated in a fabrication cluster or used in a standalone metrology setup. Therefore, the present invention should not be construed as being limited to the specific forms shown in the drawings and described above.

What is claimed:

1. A method of auto focusing a workpiece for optical metrology using an illumination beam, a focus detection beam, and a focus detector, the focus detector having a capture range, a tilt angle, a plurality of sensors, and calibration data, the method comprising:
    (a) setting the tilt angle of the focus detector wherein the focus detector is a quadrant detector, the quadrant detector having quadrants on the right hand side and quadrants on the left hand side, the quadrant detector further having lower quadrants and upper quadrants, wherein the tilt angle is set such that the focus detection beam after having moved from the lower quadrants to the upper quadrants, the focus detection beam has also shifted to the right hand side or to the left hand side of the quadrant detector and further wherein the tilt angle is set such that the focus detection beam after having moved from the upper quadrants to the lower quadrants, the focus detection beam has also shifted to the right hand side or to the left half side of the quadrant detector;
    (b) directing the focus illumination beam on the workpiece, the focus illumination beam generating the focus detection beam;
    (c) obtaining a measurement of the focus detection beam using the focus detector, the focus detection beam projecting to a location on the focus detector based on the set focus detector tilt angle and position of the workpiece on the Z-axis; and
    (d) determining two or more focus parameters derived from measurements obtained from the plurality of sensors and calibration data, the two or more focus parameters used to generate an initial position of the workpiece on the Z-axis;
    (e) if the initial position of the workpiece is not within the capture range of the focus detector, using the two or more focus parameters to move the workpiece to within the capture range of the focus detector; and iterating (b), (c), (d), and (e) until the workpiece is within the capture range of the focus detector;
    (f) if the initial position of the workpiece is within the capture range of the focus detector:
        moving the workpiece to a best focus position on the Z-axis based on at least one of the focus parameters.

2. The method of claim 1 where the workpiece is a wafer, a photomask, or a substrate.

3. The method of claim 1 wherein the focus detector tilt angle is substantially 2 degrees.

4. The method of claim 1 wherein the capture range of the focus detector is determined from a correlation of measurements from the plurality of sensors and the workpiece position on the Z-axis and wherein the correlation is linear or substantially linear.

5. The method of claim 1 wherein the capture range is determined using focus signal calculations between the upper quadrants and the lower quadrants of the quadrant detector.

6. The method of claim 1 wherein the capture range is determined using focus signal calculations between the right hand side quadrants and left hand side quadrants of the quadrant detector.

7. The method of claim 1 wherein the capture range is determined using focus signal calculations between the upper quadrants and the lower quadrants of the quadrant detector and/or determined using focus signal calculations between the right hand side quadrants and left hand side quadrants of the quadrant detector.

8. The method of claim 1 wherein moving the workpiece comprises:
   calculating a first focus parameter using a difference of a sum of focus signals of the upper quadrants from a sum of focus signals of the lower quadrants, the difference divided by a sum of all the focus signals of the quadrant detector; and
   moving the workpiece using the calculated first focus parameter.

9. The method of claim 1 wherein moving the workpiece comprises:
   calculating a second focus parameter using a difference of a sum of focus signals of the right hand side quadrants from a sum of focus signals of the left hand side quadrants, the difference divided by a sum of all the focus signals of the quadrant detector; and
   moving the workpiece using the calculated second focus parameter.

10. The method of claim 1 wherein the capture range of the focus detector is determined from a correlation of two or more focus parameters and the corresponding workpiece position on the Z-axis, the two or more focus parameters calculated from a plurality of measurements from the plurality of sensors and wherein the correlation is linear or substantially linear.

11. The method of claim 1 wherein the capture range of the focus detector is determined from a correlation of two or more focus parameters and the corresponding workpiece position on the Z-axis, the two or more focus parameters calculated from a plurality of measurements from the plurality of sensors and wherein the correlation is developed using polynomial, least squares, on non-linear regression techniques.

12. The method of claim 1 wherein the focus detector is coupled to a processor wherein the processor is part of an optical metrology system.

13. A method of auto focusing a workpiece in an optical metrology system, the method comprising:
   (a) performing auto focusing of a workpiece using an optical metrology system, the optical metrology system comprising an auto focusing subsystem, the auto focusing subsystem having a focus illumination beam, a focus detection beam, and a focus detector, the focus detector having a capture range, a tilt angle, a plurality of sensors, and calibration data, the auto focusing comprising:
      (a1) setting the tilt angle of the focus detector wherein the focus detector is a quadrant detector, the quadrant detector having quadrants on the right hand side and quadrants on the left hand side, the quadrant detector further having lower quadrants and upper quadrants, wherein the tilt angle is set such that the focus detection beam after having moved from the lower quadrants to the upper quadrants, the focus detection beam has also shifted to the right hand side or to the left hand side of the quadrant detector and further wherein the tilt angle is set such that the focus detection beam after having moved from the upper quadrants to the lower quadrants, the focus detection beam has also shifted to the right hand side or to the left half side of the quadrant detector;
      (a2) directing the focus illumination beam on the workpiece, the focus illumination beam generating the focus detection beam;
      (a3) obtaining a measurement of the focus detection beam using the focus detector, the focus detection beam projecting to a location on the focus detector based on the focus detector tilt angle and position of the workpiece on the Z-axis; and
      (a4) determining two or more focus parameters derived from measurements obtained from the plurality of sensors, the two or more focus parameters used to generate an initial position of the workpiece on the Z-axis;
      (a5) if the initial position of the workpiece is not within the capture range of the focus detector:
         using the two or more focus parameters, moving the workpiece to within the capture range of the focus detector and iterating (a2), (a3), (a4) and (a5) until the workpiece is within the capture range of the focus detector; and
      (a6) if the initial position of the workpiece is within the capture range of the focus detector:
         moving the workpiece to a best focus position on the Z-axis based on at least one of the focus parameters;
   (b) measuring a diffraction signal off a structure on the workpiece using the optical metrology system, the structure having a profile, the profile including profile parameters; and
   (c) determining at least one profile parameter of the structure using the measured diffraction signal.

14. The method of claim 13 where the workpiece is a wafer, a photomask, or a substrate.

15. The method of claim 13 wherein the capture range of the focus detector is determined from a correlation of measurements from the plurality of sensors and the workpiece position on the Z-axis and wherein the correlation is linear or substantially linear.

16. The method of claim 13 wherein the focus detector tilt angle is substantially 2 degrees.

17. The method of claim 16 wherein the capture range is determined using focus signal calculations between the right hand side quadrants and left hand side quadrants of the quadrant detector.

18. The method of claim 16 wherein the capture range is determined using focus signal calculations between the upper quadrants and the lower quadrants of the quadrant detector and/or determined using focus signal calculations between the right hand side quadrants and left hand side quadrants of the quadrant detector.

19. The method of claim 13 wherein moving the workpiece based on at least one of the focus parameters includes moving the workpiece using a motion control system, an X-Y-Z-theta stage, or a Z-stage.

* * * * *